(12) United States Patent
Fisher

(10) Patent No.: US 11,096,814 B2
(45) Date of Patent: Aug. 24, 2021

(54) APPARATUS AND METHOD FOR NON-SURGICAL TREATMENT OF PLANTAR FASCIITIS

(71) Applicant: Reid A. Fisher, New Braunfels, TX (US)

(72) Inventor: Reid A. Fisher, New Braunfels, TX (US)

(73) Assignee: Reid A. Fisher, San Antonio, TX (US)

( * ) Notice: Subject to any disclaimer, the term of this patent is extended or adjusted under 35 U.S.C. 154(b) by 340 days.

(21) Appl. No.: 16/042,781

(22) Filed: Jul. 23, 2018

(65) Prior Publication Data

US 2020/0022831 A1    Jan. 23, 2020

(51) Int. Cl.
*A61F 5/01* (2006.01)
*A61F 13/06* (2006.01)

(52) U.S. Cl.
CPC .......... *A61F 5/0111* (2013.01); *A61F 13/067* (2013.01)

(58) Field of Classification Search
CPC .... A61F 5/0111; A61F 5/0113; A61F 5/0195; A61F 5/14; A61F 13/043; A61F 13/06; A61F 13/064; A61F 13/067; A61F 2/42; A61F 2/4225; A61F 2/4606; A61F 2/66; A61F 2002/6614; A61F 5/0116; A61F 5/0127; A61F 2002/665; A61F 2007/0047; A61F 13/045; A43B 7/14; A43B 7/142; A43B 7/143; A43B 7/1495; A43B 5/0437
See application file for complete search history.

(56) References Cited

U.S. PATENT DOCUMENTS

| | | | | |
|---|---|---|---|---|
| 1,717,609 A * | 6/1929 | Ludwig | ................. | A61F 13/066 602/66 |
| 3,508,544 A * | 4/1970 | Moore | ................. | A61F 13/069 128/892 |
| 4,734,320 A * | 3/1988 | Ohira | ................. | A61F 13/0273 156/160 |
| 5,676,641 A * | 10/1997 | Arensdorf | ............. | A61F 5/0111 602/27 |
| 5,897,518 A * | 4/1999 | Shaw | ................. | A61F 5/0111 602/23 |
| 6,447,470 B2 * | 9/2002 | Bodenschatz | ......... | A61F 5/0106 602/41 |
| 6,849,057 B2 * | 2/2005 | Satou | ................. | A61F 13/0273 602/75 |
| 7,419,476 B2 * | 9/2008 | Oohira | ................. | A61F 13/066 602/23 |
| 8,216,162 B2 * | 7/2012 | Bushby | ................. | A61B 50/00 602/1 |
| 8,414,511 B2 | 4/2013 | Bushby | | |
| 8,529,483 B2 * | 9/2013 | Farrow | ................. | A61F 5/0118 602/21 |
| D691,276 S | 10/2013 | Bushby | | |
| 8,814,818 B2 * | 8/2014 | Bushby | ................. | A61F 5/0111 602/28 |
| 8,834,397 B2 | 9/2014 | Bushby | | |
| 8,834,398 B2 | 9/2014 | Bushby | | |

(Continued)

*Primary Examiner* — Tarla R Patel
(74) *Attorney, Agent, or Firm* — Conley Rose, P.C.

(57) ABSTRACT

A system and method for non-surgical treatment of plantar fasciitis is disclosed. The system comprises a primary support strap split at both ends; a secondary support strap split at one end; and a cover support strap; wherein the straps are applied to a foot such that the combination of straps provides dynamic windlass support to the foot.

24 Claims, 11 Drawing Sheets

(56) References Cited

U.S. PATENT DOCUMENTS

| | | | | |
|---|---|---|---|---|
| D795,442 S | * | 8/2017 | Arbesman | D24/189 |
| 9,833,351 B2 | * | 12/2017 | Arbesman | A61F 13/00059 |
| 10,212,987 B2 | * | 2/2019 | Bushby | A43B 7/223 |
| 10,299,953 B2 | * | 5/2019 | Bushby | A61F 13/067 |
| 2009/0182256 A1 | * | 7/2009 | Lin | A61F 13/0273 602/54 |
| 2013/0334084 A1 | * | 12/2013 | Arbesman | A61F 13/0259 206/441 |
| 2014/0107552 A1 | * | 4/2014 | Bushby | A61F 5/0111 602/28 |
| 2014/0107553 A1 | * | 4/2014 | Bushby | A43B 7/1445 602/28 |
| 2016/0106595 A1 | * | 4/2016 | Arbesman | A61F 13/00085 602/54 |
| 2017/0049629 A1 | * | 2/2017 | Arbesman | A61F 13/024 |

* cited by examiner

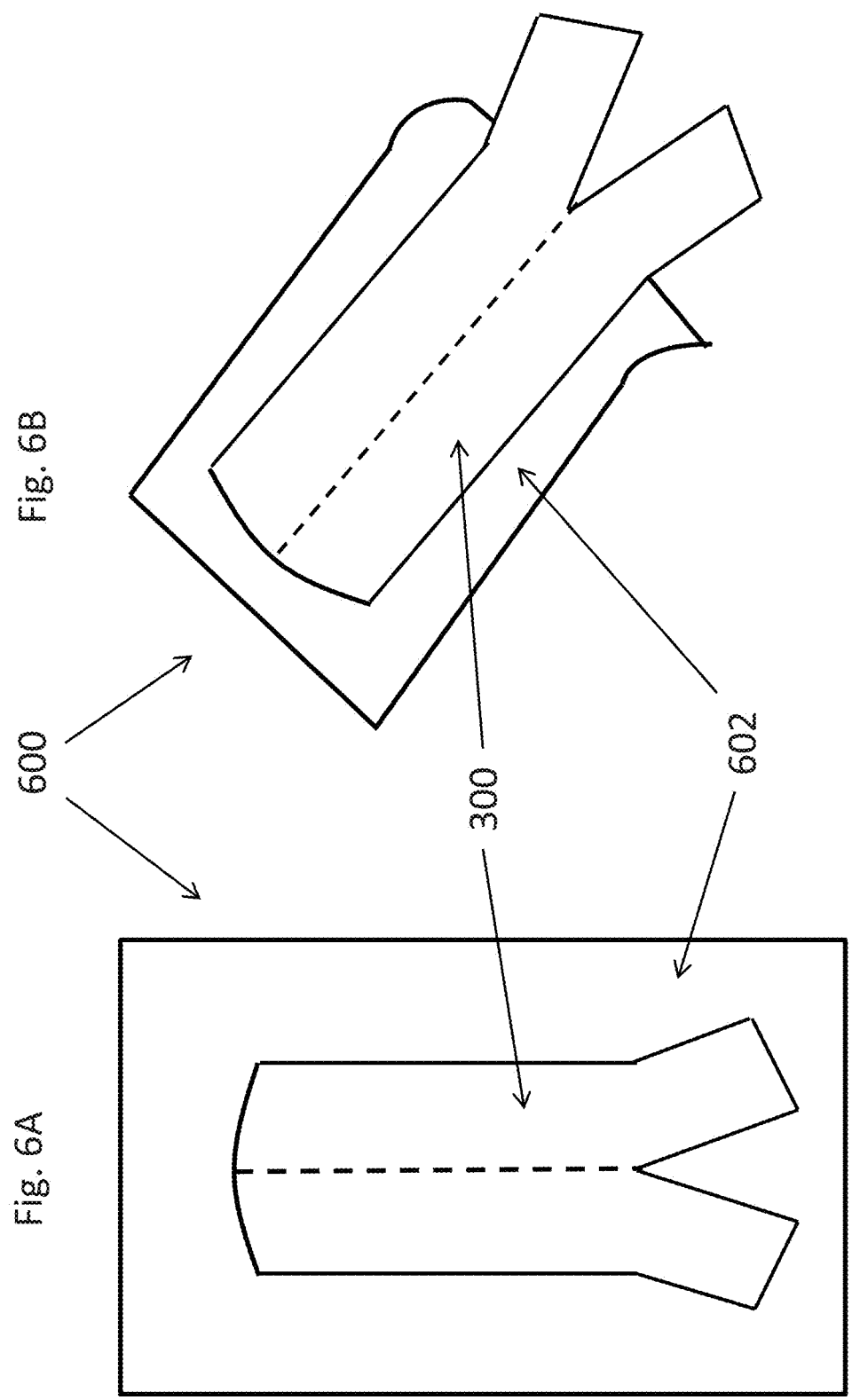

308

304

306

APPARATUS AND METHOD FOR NON-SURGICAL TREATMENT OF PLANTAR FASCIITIS

CROSS-REFERENCE TO RELATED APPLICATIONS

None.

STATEMENT REGARDING FEDERALLY SPONSORED RESEARCH OR DEVELOPMENT

Not applicable.

BACKGROUND

Plantar fasciitis (PF) is a foot condition that primarily presents as pain in the heel and in the bottom of the foot. A precise cause for the disorder is unknown but it frequently occurs in athletes, runners, in individuals who stand on hard surfaces for a long period of time, and in individuals with high arches. PF is characterized by micro tears, breakdown of collagen, and scarring of the plantar fascia at the site where the ligament attaches to the foot bone. Weight bearing activities, including standing and walking, pull on healing tissues and disrupt the formation of scar tissue in an individual with PF.

PF can be very painful, debilitating, and cause individuals to experience intense pain for months. Current treatments of PF are conservative and typically involve rest, avoiding putting weight on the injured foot, taking anti-inflammatory or pain medications and gentle stretching. More aggressive treatments include steroid injections, arch supports, or splints. It is not uncommon for the disorder to last six months or longer. Most individuals do not experience any pain relief, even with treatment, for several weeks or longer. There is a need for better treatment that can alleviate pain quickly, that permits the plantar fascia to heal quickly, and that can function as a long term solution.

SUMMARY OF THE DISCLOSURE

In an embodiment, a system for non-surgical treatment of plantar fasciitis is disclosed. The system comprises a primary support strap split at both ends; a secondary support strap split at one end; and a cover support strap; wherein the straps are applied to a foot such that the combination of straps provides dynamic windlass support to the foot.

A method of non-surgical treatment for of plantar fasciitis is disclosed. The method comprises applying a primary support strap to a foot, wherein a distal end of the primary support strap is placed at the metatarsal phalanges joint near the toes, the primary support strap is adhered along the length of the foot, and a proximal end of the primary support strap is placed near the heel; applying a secondary support strap to a foot, wherein the distal end of the secondary support strap is applied across the metatarsal phalangeal joints at the ball of the foot, the secondary support strap is adhered along the length of the foot, and a proximal end of the secondary support strap is placed at the heel; and applying a cover support strap to a foot, wherein the cover support strap is tensioned and adhered across the metatarsal phalanges joint in a direction perpendicular to the primary and secondary support straps.

A method of non-surgical treatment for of plantar fasciitis is disclosed. The method comprises applying a primary support strap to a foot, wherein a distal end of the primary support strap is placed at the metatarsal phalanges joint near the toes, the primary support strap is adhered along the length of the foot, and a proximal end of the primary support strap is placed near the heel; applying a secondary support strap to a foot, wherein the distal end of the secondary support strap is applied across the metatarsal phalangeal joints at the ball of the foot, the secondary support strap is adhered along the length of the foot, and a proximal end of the secondary support strap is placed at the heel; applying a cover support strap to a foot, wherein the cover support strap is tensioned and adhered across the metatarsal phalanges joint in a direction perpendicular to the primary and secondary support straps; wearing the support straps for a period of at least one month; and replacing the supports straps every three to four days.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 6A is an illustration of a component of a system according to an embodiment of the disclosure.

FIG. 6B is an illustration of a component of a system according to an embodiment of the disclosure.

DETAILED DESCRIPTION OF DISCLOSED EXEMPLARY EMBODIMENTS

Figure 1:
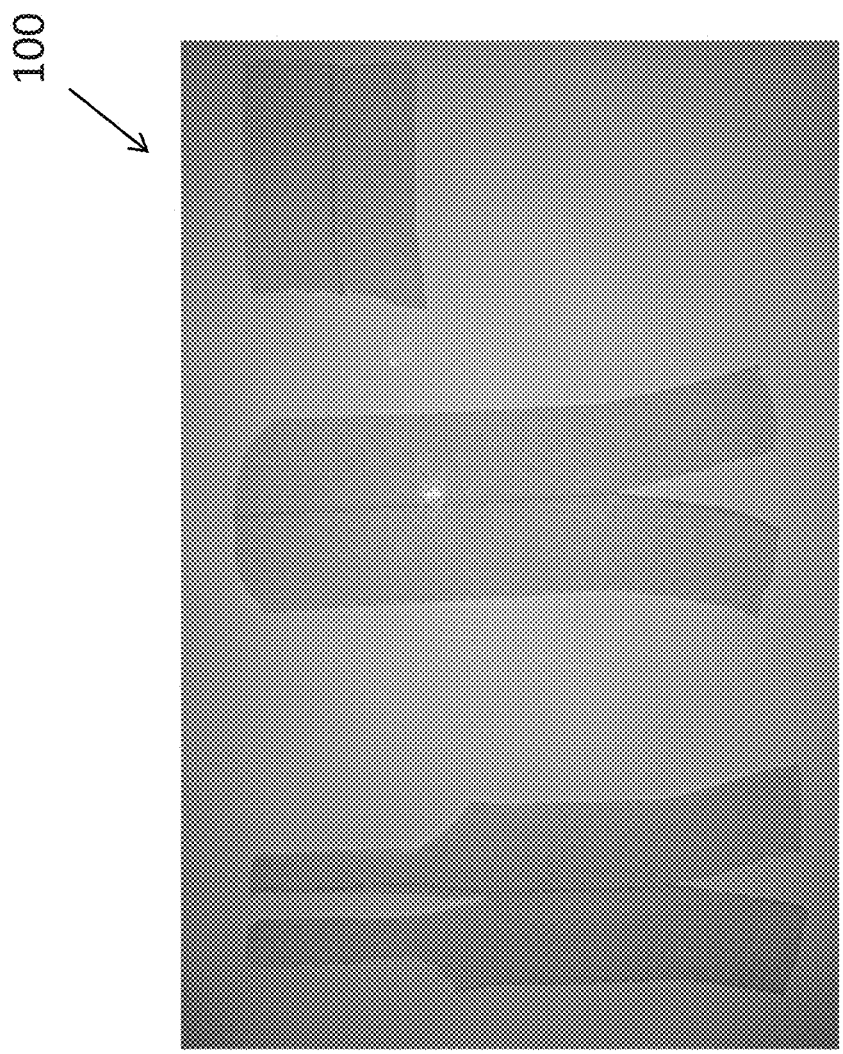
FIG. 1 is an illustration of a system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The plantar fascia is a tendinous band of collagen fibers that stretch from the medial tubercle of the calcaneus to the heads of each of the five metatarsal bones. These osseous landmarks represent the endpoints of the medial longitudinal arch. The proximal attachment of the plantar fascia runs continuous through fascial fibers with the distal attachment of the Achilles tendon. Creating tension through contraction of the calf muscles can increase tension in the plantar fascia.

During gait, the foot transitions through various stages of support. In early stages from heel strike to midstance, the medial longitudinal arch receives and assists absorption of the body's weight. Donatelli, R., "Normal biomechanics of the foot and ankle." *J. Orthopedic Sports Phys Ther.*, 1985; 7(3):91-95, describes the windlass mechanism that tensions the plantar fascia to increase rigidity of the foot as one progresses from midstance to heel off and ultimately toe-off. The tensioning load of the plantar fascia bows the medial longitudinal arch and augments rigidity to turn the supple force-dampening arch into a lever for propulsion. As such the arch serves to both absorb biomechanical stresses as well as function as a rigid lever over which the body can generate forward momentum in walking.

For reasons not fully identified within the literature, the plantar fascia can become irritated making gait a painful endeavor. This conditioned is termed, perhaps erroneously, as plantar fasciitis (PF), or inflammation of the plantar fascia. During the transition to heel off in the gait cycle, the windlass mechanism requires significant strain to be placed on the plantar fascia tissue. If microscopic tears exist from repetitive overuse then the cyclical strain from walking competes with the body's natural repair mechanism, the inflammatory response. LeMelle, Kisilewicz and Janis found evidence of inflammation in chronic sufferers of PF (LeMelle D P, Kisilewicz P, Janis L R, "Chronic plantar fascial inflammation and fibrosis." *Clin Podiatr Med Sur*, 1990; 7:385-9) but a separate review of fifty cases of heel spur surgery found none. Lemont H, Ammirati, Usen. "Plantar Fasciitis" *J Amer Pd Med Assoc*, 2003; 93(3): 234-237. Lemont, Ammirati, and Usen contend that PF is a degeneration that occurs without the inflammatory process. Others have identified thickening of the tissue that correlates with patient reports of pain implying some kind of reactive, albeit ineffective, healing response is ongoing. See Fabrikant J M, Park T S. "Plantar fasciitis (fasciosis) treatment outcome study: plantar fascia thickness measured by ultrasound and correlated with patient self-reported improvement." *Foot (Edinb).* 2011; 21:79-83; Wearing S C, Smeathers J E, Sullivan P M, Yates B, Urry S R, Dubois P. "Plantar fasciitis: are pain and fascial thickness associated with arch shape and loading?" *Phys Ther.* 2007; 87:1002-1008; Wu C H, Chang K V, Mio S, Chen W S, Wang T G. "Sonoelastography of the plantar fascia." *Radiology.* 2011; 259:502-507.

Cook and Purdam have suggested a continuum of reactive change that skips inflammatory intermediaries leading to degeneration in response to biomechanical loads. Cook J, Purdam C R. "Is tendon pathology a continuum? A pathology model to explain the clinical presentation of load-induced tendinopathy." *Br J Sports Med* 2009; 43:409-16. They specifically proposed their pathology-driven approach in reference to tendinopathies, but their reasoning could reflect fascial changes as well.

For the patient, the first step of the morning, or after any prolonged period of unloading to the medial longitudinal arch, induces significant pain. Long periods of standing and walking, especially as the heel lifts from the ground aggravate the primary complaints. Disability and avoidance of activity secondary to fear have been well-documented. Lentz T A, Sutton Z, Greenberg S, Bishop M D. "Pain-related fear contributes to self-reported disability in patients with foot and ankle pathology." *Arch Phys Med Rehabil.* 2010; 91:557-561.

In a meta-analysis of research looking at a pooled sampling of 3,500 runners, Lopes found incidence rates of 4.5-10% and a prevalence between 5.2-17.5%. Lopes A D, Hespanhol Junior L C, Yeung S S, Costa L O. "What are the main running-related musculoskeletal injuries? A systematic review." *Sports Med.* 2012; 42: 891-905. In a prospective study of 166 runners, Di Caprio reported 31% as developing PF. Di Caprio F, Buda R, Mosca M, Calabró A, Giannini S. "Foot and lower limb diseases in runners: assessment of risk factors." *J Sports Sci Med.* 2010; 9:587-596. For those unfortunate enough to fall victim to PF, the average persistence of symptoms lasts over 13 months. Klein S E, Dale A M, Hayes M H, Johnson J E, McCormick J J, Racette B A. Clinical presentation and self-reported patterns of pain and function in patients with plantar heel pain. *Foot Ankle Int.* 2012; 33:693-698; Yi T I, Lee G E, Seo I S, Huh W S, Yoon T H, Kim B R. "Clinical characteristics of the causes of plantar heel pain." *Ann Rehabil Med.* 2011; 35:507-513. PF impacts a large number of people resulting in pain and disability for a considerable amount of time.

The ongoing debate about the presence or absence of inflammatory markers in conjunction with PF provides a clue as to the inability of healthcare practitioners to resolve the symptoms in less than a year. A first round intervention involves the immediate beginning of non-steroidal anti-inflammatory drugs (NSAIDS). If tissue degeneration occurs in the absence of inflammation then the NSAIDS serve little purpose. When NSAIDS fail to relieve the pain, practitioners move towards steroid injections, selected for the purpose of stopping inflammation. Two systematic reviews failed to support their use. Landorf K B, Menz H B. "Plantar heel pain and fasciitis." *Clin Evid* (Online) 2008; 2008:1111; Uden H, Boesch E, Kumar S. "Plantar fasciitis—to jab or to support? A systematic review of the current best evidence." *J Multidiscip Healthc.* 2011; 4:155-164.

In a large review of best practices, Martin et al. came to the conclusion that most modalities used in clinical practice by physical therapists were of little to no benefit. Martin et al. "Heel pain—plantar fasciitis: Revision 2014." *J of Orthop Sports Phys Ther.* 2014; 44(11):A1-A23. Extracorporeal shockwave therapy, dry needling, and ultrasound demonstrated ineffectiveness. Phonophoresis, low-level laser therapy, and iontophoresis presented statistically significant, but clinically limited results. The final recommendations encouraged the use of manual therapy to improve joint and soft-tissue mobility, stretching, and splinting the arch to unload the plantar fascia.

Splinting can take several forms. Low-dye arch taping procedures with athletic tape more directly attempt to limit arch collapse during midstance and stabilize this transition. Two studies, one by van de Water and Speksnijder, and the other by Landorf and Menz, found significant pain reduction for short durations with arch-supportive taping procedures. van de Water A T, Speksnijder C M. "Efficacy of taping for the treatment of plantar fasciosis: a systematic review of controlled trials." *J Am Podiatr Med Assoc.* 2010; 100:41-51; Landorf K B, Menz H B. "Plantar heel pain and fasciitis." *Clin Evid* (Online) 2008; 2008:1111. No improvement in function or disability measures were found.

For those who experienced benefits in taping, orthotics, either custom-fit or over-the-counter, can help provide rigidity to the arch and unload the plantar fascia during the windlass mechanism. The orthotic takes on as much as 34% of the load of supporting the medial longitudinal arch in the transition to the fulcrum and lever arm necessary for propulsion during gait. Ferber R, Benson B. "Changes in multi-segment foot biomechanics with a heat-mouldable semi-custom foot orthotic device." *J Foot Ankle Res.* 2011; 4:18. Examples of orthotic devices used to treat plantar fasciitis can be found in U.S. Pat. Nos. 8,216,162; 8,414,511; and 8,834,397.

Investigators Meier, McPoil, Cornwall, and Lyle reported significant reduction in pain for short-term use of orthotic devices. Meier K, McPoil T G, Cornwall M W, Lyle T. "Use of antipronation taping to determine foot orthoses prescription: a case series." *Res Sports Med.* 2008; 16:257-271. For long-term sufferers (over 4 months), splinting the foot at night while sleeping seems to reduce the early-morning pain experienced upon the first steps out of bed. Martin et al. "Heel pain—plantar fasciitis: Revision 2014." *J of Orthop Sports Phys Ther.* 2014; 44(11):A1-A23.

Standard low dye arch taping techniques have been found to be limited in their effectiveness because the tape lost all tension and stretched within ten minutes of walking and provided no support for running. Vicenzino redeveloped a standard low-dye taping technique into an augmented low-dye procedure that uses a more stretch-resistant tape and incorporates straps that cross the ankle mortise. Vicenzino B. "Foot orthotics in the treatment of lower limb conditions: a musculoskeletal physiotherapy perspective." *Man Ther.* 2004; 9:185-196. This augmented taping procedure provided support through 20 minutes of running and was found to be effective for up to three weeks at reducing patient symptoms. Other examples of stretch resistant taping products and methods used to treat PF can be found in U.S. Pat. Nos. 8,814,818; 8,834,398; and 8,968,229.

Stretching of the plantar fascia has demonstrated pain relief for short-term management (2 weeks-4 months). Beyond this point little information exists to support its use. Increasing the load to plantar fascia would seem to increase the biomechanical strain already present during gait. This approach seems somewhat counterintuitive towards protecting tissues actively trying to heal. Cook and Purdam (Cook J, Purdam C R. "Is tendon pathology a continuum? A pathology model to explain the clinical presentation of load-induced tendinopathy." *Br J Sports Med* 2009; 43:409-16) have hypothesized that some form of healing mechanism is ongoing while acknowledging the biomechanical loads outlined by Donatelli. Donatelli R. Normal biomechanics of the foot and ankle. *J of Orthop Sports Phys Ther.* 1985; 7(3):91-95.

A conclusion that can be drawn from existing research and treatments for PF is that it is paramount, when employing a non-surgical intervention, to use a treatment that includes a dynamic release that supports the envelope of function in the altered state of injury. The therapeutic approach must decrease the load and/or frequency of load to a level that permits healing to commence in the foot. The persistence of pain and disability result in the load that is involved in the windlass mechanism during normal gait that exceeds limits of healing tissue.

A novel elastic, self-adhesive tape support system and method for treating PF is disclosed. According to various embodiments, a stepwise application of elastic, adhesive straps to the plantar surface of the foot to dynamically unload the plantar fascia (PF) is disclosed. The straps are elastic, but have a clear maximal stretch capacity at which point the strap no longer permits expansion. One strap (primary) serves to pull the distal metatarsal phalangeal (MTP) joints (distal attachment of the PF) towards the calcaneus proximally. A second primary strap (secondary strap) may be applied depending on the degree of unloading required. The proximal attachment bifurcates at the calcaneal tuberosity and wraps over the posterior calcaneus in an overlapping fashion. A third strap (cover) serves to cover the MTP joints transversely and wrap to dorsal surface as a cover to the primary and secondary straps, thereby preventing slippage. The dual nature of the strapping (elastic to a point) mimics the normal physiological actions of the PF. The elastic component absorbs the normal tensile load created during weight bearing. The terminal stretch endpoint then enables greater unloading of the PF during the increased tensioning during heel off, the Windlass mechanism.

According to several embodiments, the elastic, self-adhesive tape support system works by mimicry of the plantar fascia in both the loading phases and the production of tension, the Windlass mechanism. During weight-bearing and the loading phase of gait, the plantar fascia stretches allowing the ends of the medial longitudinal arch of the foot to settle and extend. Significant tension is produced as the plantar fascia limits this distracting force. As the heel lifts off during gait in preparation for the swing phase, the toes extend which rotates the MTP joint away and pulls the distal attachment of the plantar fascia from its origin resulting in increased tension. The tensioning of the plantar fascia draws the ends of the medial longitudinal arch towards each other turning the foot into a rigid lever. The elastic, self-adhesive tape support system that has an extension up the length of the big toe further supports the windlass mechanism and can unload toe flexion stress allowing for healing to occur.

A descriptive analogy would be the increased tension and curvature produced in the shaft of a bow when an arrow draws the string back. The increased rigidity allows the previously supple arch to now serve as the fulcrum through which the person can leverage force for propulsion. When injured, the stretch on the plantar fascia during weight bearing pulls on healing tissues disrupting scar tissue. The subsequent pull from the Windlass mechanism at heel off places increased tensile forces yielding increased disruption of scar tissue. By the application of an elastic, adhesive strap, the absorptive nature of the plantar fascia during weight acceptance is facilitated which minimizes strain and protects the healing tissues. The elastic, self-adhesive tape support system still allows for some natural elastic movement in the PF affected tissue. As a result, nutrients that are necessary for healing are able to be delivered to the injured site as the cycle of stretch and relax encourages fluid movement. The terminal endpoint of stretch in the fabric allows the plantar fascia to be unloaded from the burden of creating the rigidity necessary to leverage off of the foot in the propulsion stage of gait. The combination of elasticity and rigidity closely mimics the normal function of the plantar fascia such that an optimal unloading can occur, minimizing pain and encouraging healing.

EXAMPLE

The presently disclosed subject matter is further illustrated by the following specific but non-limiting example.

According to an embodiment, the elastic, self-adhesive tape support system to treat PF disclosed herein has shown to be effective in reducing and alleviating pain from PF within three days. An alternative diagnosis to PF is a strain in the flexor digitorum *brevis* muscle or tendinopathy of the flexor hallicus longus. This taping procedure has demonstrated to further reduce pain in these conditions as well.

A research study was performed with the purpose of assessing the effectiveness of the elastic, self-adhesive tape support system against other conditions, low-dye taping and a control, and to assess the effectiveness at reducing pain and disability associated with PF.

Materials and Methods. The study was coordinated with a podiatrist in New Braunfels, Tex. Research interventions were performed on patients around the patient's schedules, 2-3 times per week for three weeks. The elastic self-adhesive tape used was Elastikon, a top-tier athletic tape manufactured by Johnson & Johnson, New Brunswick, N.J. and sold through a sports medicine vendor.

Subjects and Informed Consent. Study subjects were individuals who have been diagnosed with PF. Upon seeking medical care from a local podiatrist for heel and/or foot related pain, the diagnosis was made using inclusion criteria that has been substantiated by Martin et al. in a meta-analysis. Martin et al. "Heel pain—plantar fasciitis: Revision 2014." *J of Orthop Sports Phys Ther.* 2014; 44(11): A1-A23. These criteria are

- Plantar medial heel pain: most noticeable with initial steps after a period of inactivity but also worse following prolonged weight bearing
- Heel pain precipitated by a recent increase in weight-bearing activity
- Pain with palpation of the proximal insertion of the plantar fascia
- Positive windlass test
- Negative tarsal tunnel tests
- Limited active and passive talocrural joint dorsiflexion range of motion Subjects who were within 8 weeks of receiving a cortisone injection were excluded from study participation.

Patients who meet the parameters of the study with a diagnosis of PF were recruited to the study. Interested individuals were given a notification sheet introducing the principal investigator (PI) of the study and that invited them to directly call or show for a group informational meeting held once a week. The PI discussed the purpose and procedures of the research study and the two treatment techniques that were to be employed. All subjects continued with the treating physician's normal, evidence-based suggestions for managing PF, including foot intrinsic strengthening, stretching, and cryotherapy. The subjects were free to end participation of the study at any time without risk of reprisal. If a subject's pain level was not significantly ameliorated at the end of the initial three-week experimental phase, an alternate solution was offered. The subjects received no compensation for participating in the study.

Study Length. The study lasted for about 18 months. Eight subjects participated. Six were diagnosed with plantar fasciitis and two others with flexor digitorum *brevis* strains. Each subject was asked to participate in assessing the intervention for a period of three weeks. Data reflecting the results of the effects of short-term taping effects was collected once a week throughout the taping duration. The subjects each had a follow-up visit at one month and six months from the beginning of their participation. The follow-up visits identified short and long-term impacts of the treatments.

Study Design. The subjects received the new taping method, Dynamic Windlass Support (DWS) according to embodiments disclosed herein, which aimed to dynamically unload the arch using Elastikon. After initial application, a follow-up appointment was held to apply (or reapply) the tape procedures that were expected to remain on the patient until the next appointment (a 3-4 day span). Retaping procedures were done every four days.

DWS Application. Subjects in the DWS group received the following method of tape application. First, the foot is cleaned and dried. No oils or lotion are permitted to be applied. The backing from the primary strap is removed and the distal end of the primary strap is affixed along the base of the toes beginning under the edge of the big toe and working towards the little toe. The MTP joints along the ball of the foot are massaged to endure a solid attachment. A gentle pull is used on the proximal split ends of primary strap and the split ends are loosely affixed to the sides of the heel. Next, the backing from the secondary strap is removed. The point of separation of the distal end split ends is aligned to the mid-point of the ball of the foot. Using a slight tension, one distal split end is wrapped around the big toe side to the foot and the other distal split end is wrapped around the small toe side to the top of the foot. The distal split ends may overlap but it is not necessary. The straps are massaged from the ball of the foot around to the top of the foot to secure the attachment. The proximal split ends of secondary strap are pulled with slight tension, aligned around the heel with the primary strap and affixed to the sides of the heel on top of the primary strap ends. Last, the cover strap is aligned sideways (perpendicular) to the primary and secondary straps. Using moderate tension, the cover strap is affixed along the base of the toes from the middle toes and wrapped outwards toward the big and little toes ending on the top of the foot. The entire cover strap is massaged to ensure adhesion to the foot. The elastic, self-adhesive tape support system of this disclosure can be adjusted quickly and simply to tighten or release pressure. To tighten the straps, the heel straps are first released and the foot should be completely relaxed. The small toe side straps are then pulled taut from the outside (lateral) to the inside (medial). Then the big toe side straps are pulled very taut and wrapped from the inside (medial) to the outside (lateral). The DWS tape application is left in place and changed every 3 to 4 days.

Data Collection. Four categories of data were collected.
- self-described pain related to particular activities;
- impacts on normal daily activities (disability index);
- measures of daily activity through step-counts; and
- clinical measures of pain.

The first two categories were assessed using the Foot Function Index (FFI) which has been suggested by Martin et al. to produce quantitative measures of pain and disability. Step counts were assessed with a pedometer given to each participant. Clinical measures of pain were done using an algometer. The algometer allows for consistent and measured pressure loads to be applied to the bottom of the foot with pain responses by the subject given on a visual analog scale of 0-10 spread over a 100 mm line.

Upon subject consent, the subjects met with the PI to receive the first tape application. The first application remained on the subject until it could be reapplied, about every 3-4 days. The data collection lasted for three weeks. The subject was asked to complete a new FFI and algometer assessment each session.

The FFI contains 17 questions, each asking for a response on a visual analog scale of 0-10. The result yields a composite score based on 170 points. Subjects reported total step counts within a day and steps by time of day. The algometer was clinically applied right after an old tape application has been removed but before a new one has been applied. All subjects used a specific code to blind the PI from group response membership during analysis. All statistical analyses were assessed by repeated measure analysis of variance using SPSS.

All subjects received the physician's standard of care including recommendations for stretching, exercise, ice, NSAIDS, and footwear accommodation. Subjects received the new taping method according to an embodiment disclosed herein and not previously studied in the literature.

A slight risk of skin irritation was present. Subjects were asked if they had any known allergy to adhesive tape. Additionally, the tape products have a tendency to leave an adhesive residue on the skin that may be annoying to the subject so the subjects were directed to remove the tape if any pruritic reactions occurred.

Study Results. Because of the low enrollment numbers statistical comparisons were not performed. All six subjects diagnosed with plantar fasciitis experienced complete abatement of pain associated with the first step in the morning within 2 to 3 days of the first application. Three subjects experienced complete pain relief within the first day after application. Further, three of the six subjects diagnosed with plantar fasciitis experienced an absence of all symptoms of PF, indicating a healing of the PF, within a three week period after initial treatment. Both patients with flexor digitorum brevis muscle strains presented with immediate pain relief, but did not fully heal by the end of three weeks.

FIG. 1 is an illustration of a tape support system 100 according to embodiments of the present disclosure. In the system 100, primary strap 200, secondary strap 300, and cover strap 400 are composed of a soft cotton elastic tape material that contains an adhesive backing. The soft cotton elastic tape can be made of Elastikon® Elastic Tape, Johnson & Johnson, New Brunswick, N.J., Mueller Stretch MTape®, Mueller Sports Medicine, Inc., Prairie du Sac, Wis., or any similar elastic material. The adhesive utilized on the tape can be any type of suitable consumer adhesive regularly used in sports medicine and physical rehabilitation settings for the express purpose of attachment to the skin. Such adhesive may be available from companies such as Bostik, Inc., Wauwatosa, Wis., or other suitable vendor. In an embodiment, the soft elastic cotton tape 100 contains an adhesive and is affixed to a backing paper that must be removed prior to use.

Figure 2:
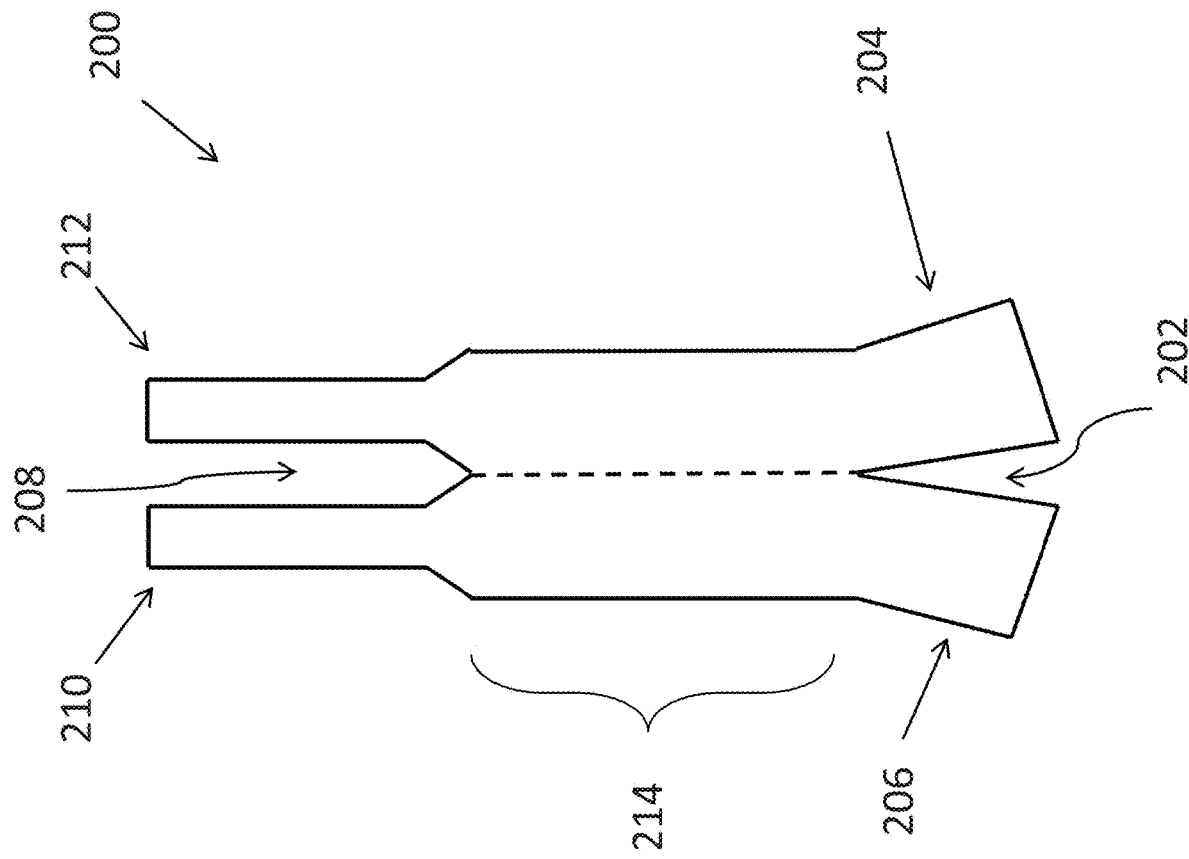
FIG. 2 is an illustration of a component of a system according to an embodiment of the disclosure.

FIG. 2 illustrates a primary strap 200 according to an embodiment of the disclosure. Primary strap 200 contains a proximal end split 202 that separates the 4 inch strap 200 into two halves 204 and 206, each 2 inches in width. The length of the separation cut at proximal end split 202 is 2 inches. The distal end of primary strap 200 is cut at the midpoint, creating a distal end split 208, and creating two smaller strip ends 210 and 212 with beveled edges. The middle zone 214 of secondary strap 200 is located approximately 2.5 inches from the confluence of the proximal split ends to the confluence of the distal split ends. Primary strap 200 can also be made in small, medium and large lengths to accommodate different patient's foot lengths. A small primary strap 200 may measure anywhere between 6 inches and 8 inches in length and 4 inches in width. A medium primary strap 200 may measure anywhere between 8 inches and 10 inches in length and 4 inches in width. A large primary strap 200 may measure anywhere between 10 inches and 13 inches in length and 4 inches in width. An extra-large primary strap 200 may measure greater than 13 inches in length and 4 inches in width.

Figure 3:
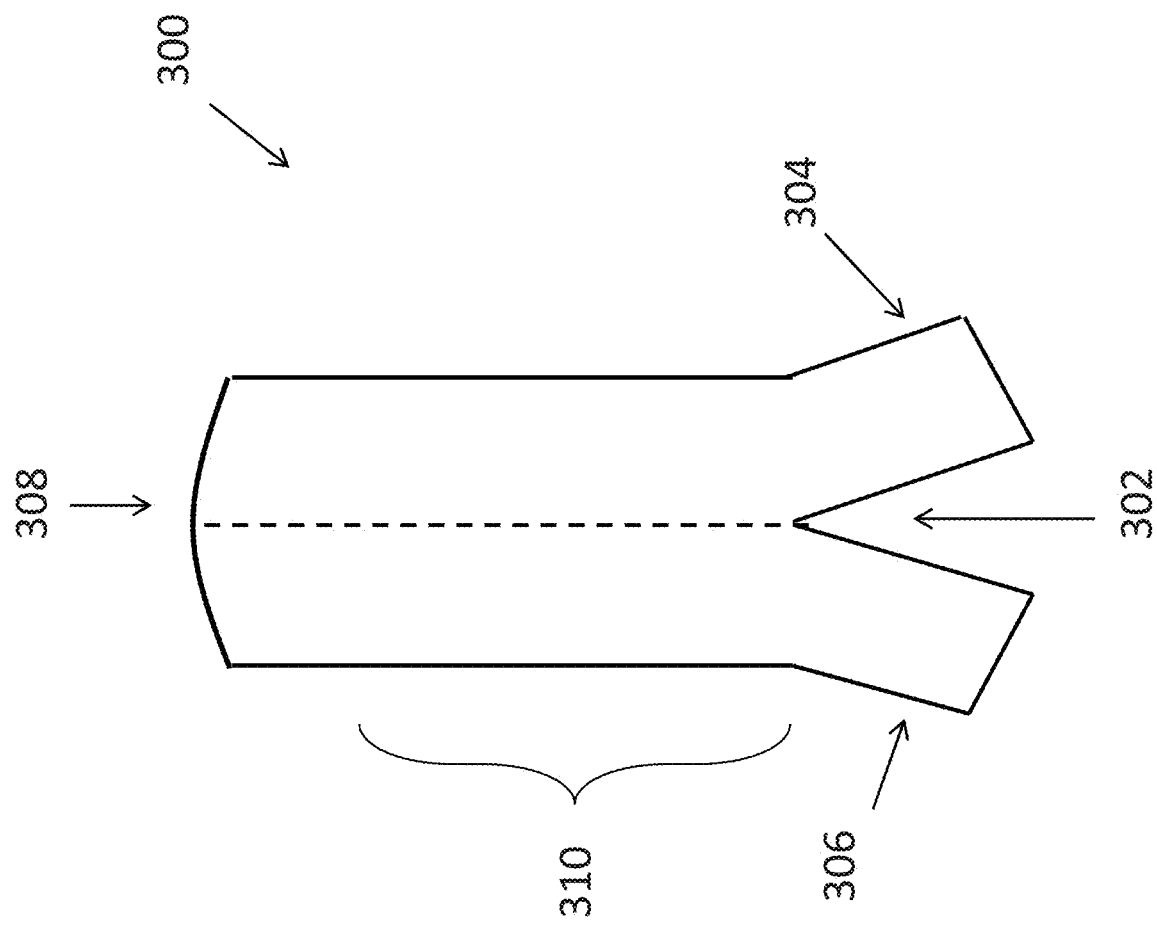
FIG. 3 is an illustration of a component of a system according to an embodiment of the disclosure.

FIG. 3 illustrates a secondary strap 300 according to an embodiment of the disclosure. Secondary strap 300 is generally composed of a four inch wide soft cotton elastic tape that also contains an adhesive backing. An ideal length of secondary strap 300 is the length of the patient's foot. Accordingly, secondary strap 300 can be made in small, medium and large lengths to accommodate different patient's foot lengths. A small secondary strap 300 may measure anywhere between 6 inches and 8 inches in length and 4 inches in width. A medium secondary strap 300 may measure anywhere between 8 inches and 10 inches in length and 4 inches in width. A large secondary strap 300 may measure anywhere between 10 inches and 13 inches in length and 4 inches in width. An extra-large secondary strap 300 may measure greater than 13 inches in length and 4 inches in width.

Secondary strap 300 contains a proximal end split 302 that separates the 4 inch strap 300 into two halves 304 and 306, each 2 inches in width. The distal end 308 of secondary strap 300 is curved to match the curvature of the metatarsal phalangeal joints along the base of the toes. The middle zone 310 of secondary strap 300 is located approximately 2.5 inches from the confluence of the split ends to the proximal start of the ball of the foot.

Figure 4:
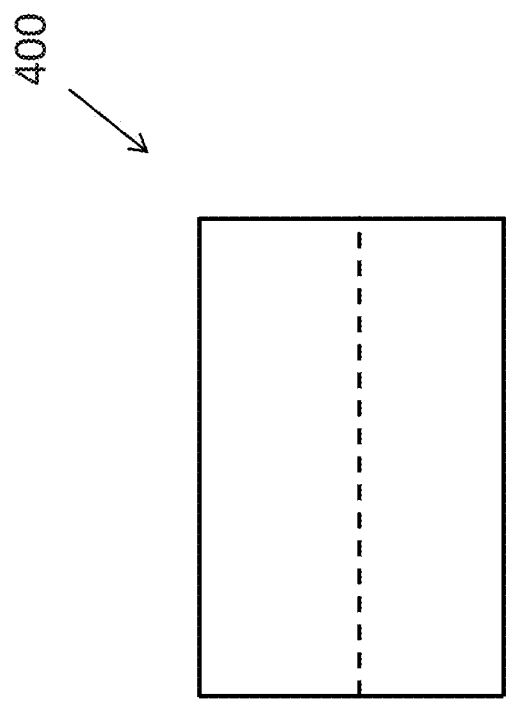
FIG. 4 is an illustration of a component of a system according to an embodiment of the disclosure.

FIG. 4 illustrates a cover strap 400 according to an embodiment of the disclosure. Cover strap 400 can be of varying lengths but is typically shorter in length than the primary strap 200 or secondary strap 300. A small cover strap 400 may measure anywhere between 5 inches and 6 inches in length and 4 inches in width. A medium secondary strap 300 may measure anywhere between 6 inches and 7 inches in length and 4 inches in width. A large secondary strap 300 may measure anywhere between 7 inches and 8 inches in length and 4 inches in width. An extra-large secondary strap 300 may measure greater than 8 inches in length and 4 inches in width.

Figure 5B:
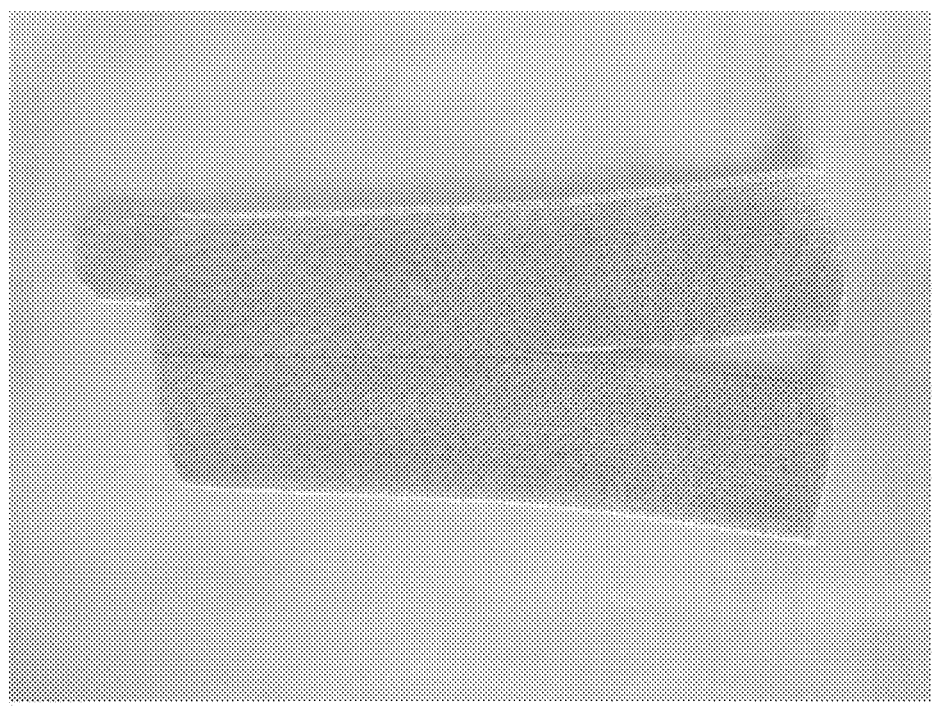
FIG. 5 is an illustration of a component of a system according to an embodiment of the disclosure.
Figure 5A:
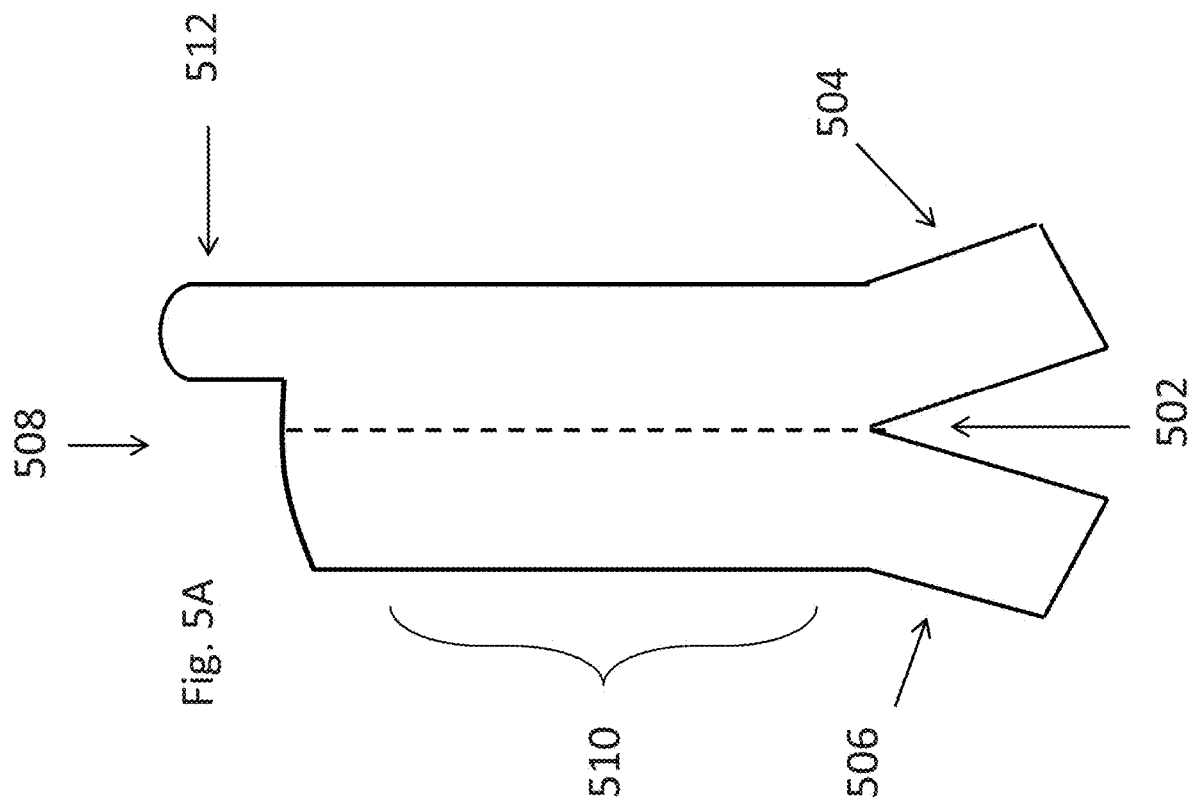

FIG. 5 illustrates a secondary strap 500 according to an alternative embodiment. Secondary strap 500 is generally composed of a four inch wide soft cotton elastic tape that also contains an adhesive backing. Secondary strap 500 contains a proximal end split 502 that separates the 4 inch strap 500 into two halves 504 and 506, each 2 inches in width. The distal end 508 of secondary strap 500 is partially curved to match the curvature of the metatarsal phalangeal joints along the base of the toes. The middle zone 510 of secondary strap 500 is located approximately 2.5 inches from the confluence of the split ends to the proximal start of the ball of the foot. Distal end 508 contains a toe strap 512 that extends from the distal end of the strap and that covers the big toe to further support the windlass mechanism and unload toe flexion stress that allows for healing to occur.

FIGS. 6A and 6B show a support strap affixed to backing paper 600 according to an embodiment of the disclosure. FIGS. 6A and 6B illustrate a secondary strap 300 affixed to backing paper 602. FIG. 6A shows the secondary strap 300 affixed to backing paper 602 intact. FIG. 6B shows the secondary strap 300 affixed to backing paper 602 where the backing paper 602 is in the process of being peeled off the secondary strap 300. All support straps disclosed herein can be prepared in a similar way as affixed to backing paper that is to be peeled off before use.

Figure 7A:
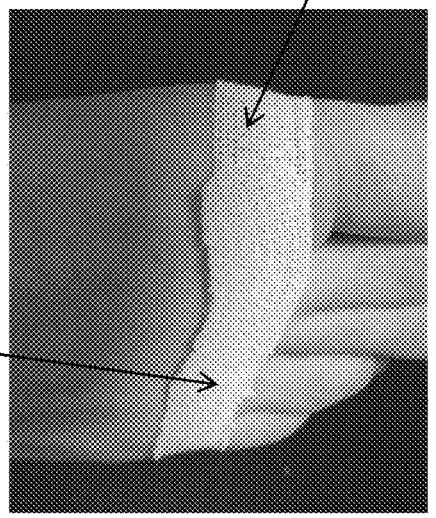
FIGS. 7A, 7B, and 7C are illustrations of steps in the application of a system according to an embodiment of the disclosure.
Figure 7B:
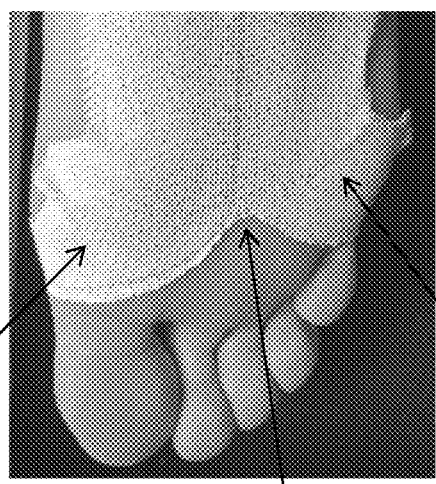
Figure 7C:
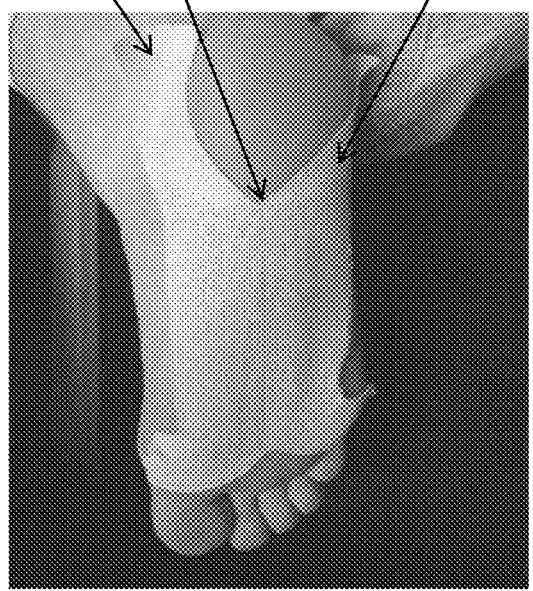

FIGS. 7A-C illustrate the first step in the method of application of application of tape support system 100 according to embodiments of the disclosure. FIGS. 7A and 7B show the application of primary strap 200. The distal end of primary strap 200 is applied in the direction of toes to heel, with distal end split 208 applied close or at the MTP joint. The distal end straps 210 and 212 are wrapped distal to the MTP joint and overlaid across the top of the foot as seen in FIG. 7B. FIG. 7C shows proximal end split 202 of primary strap 200 adhering to the foot at approximately above the ball of the foot. Proximal split ends 204 and 206 are gently tensioned and loosely stuck to the sides of the calcaneus.

Figure 8C:
FIGS. 8A, 8B, and 8C are illustrations of steps in the application of a system according to an embodiment of the disclosure.
Figure 8A:
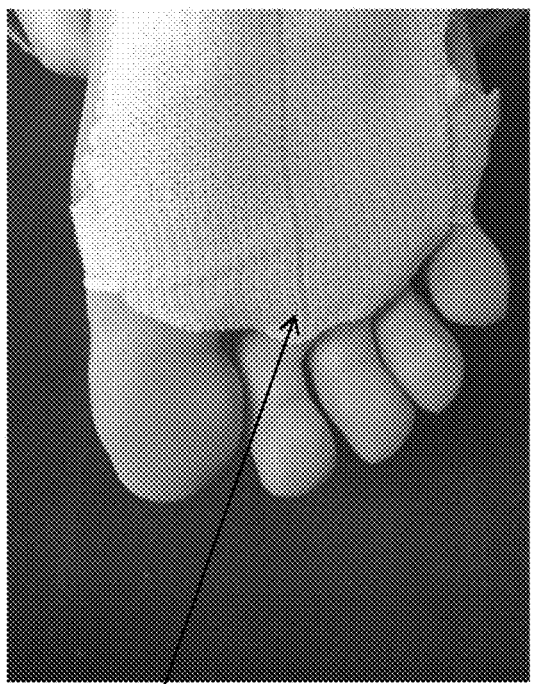
Figure 8B:
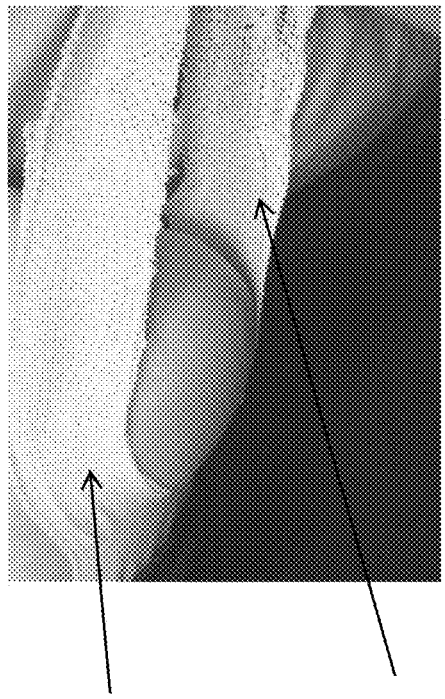

FIGS. 8A-C illustrate the second step in the method of application of application of tape support system 100 according to embodiments of the disclosure. FIG. 8A shows the application of secondary strap 300 in the direction of toes to foot. Curved distal end 308 is applied to the ball of the foot, across the MTP joints and similarly tensioned to match primary strap 200. FIG. 8B shows the proximal split ends 304 and 306 overlaid across the heel. While the foot is relaxed and the ankle is plantarflexed, the proximal split ends 304 and 306 are tensioned as desired and overlaid across the heel as shown in FIG. 8C.

Figure 9B:
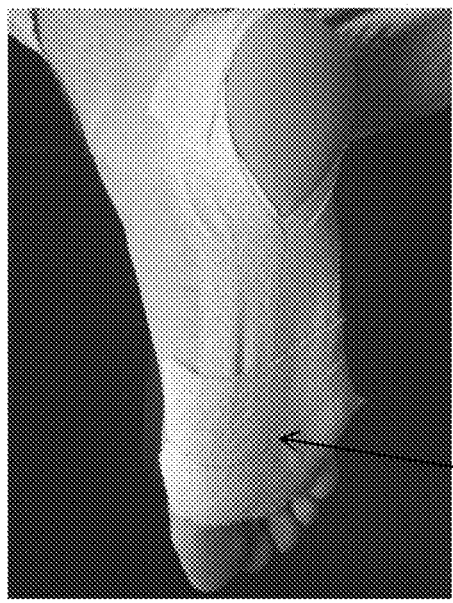
FIGS. 9A and 9B are illustrations of steps in the application of a system according to an embodiment of the disclosure.
Figure 9A:

FIG. 9A demonstrates the completed application of the primary strap 200 and secondary strap 300. FIG. 9B shows the application of cover strap 400 according to an embodiment of this disclosure. Cover strap 400 is fully tensioned and laid over the MTP joints in a direction perpendicular to primary strap 200 and secondary strap 300. The entire length of cover strap 400 is massaged to ensure maximal attachment.

Figure 10:
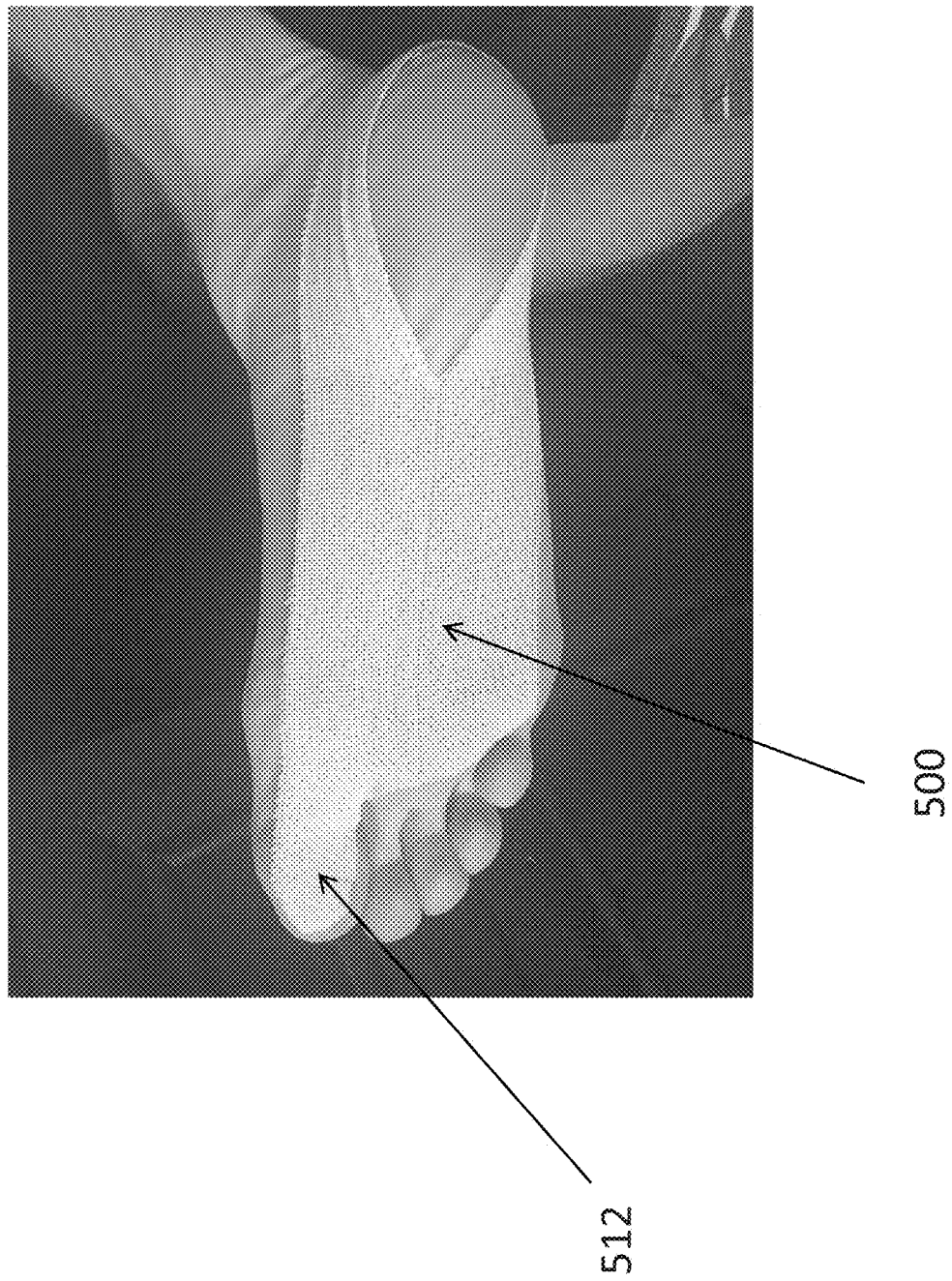
FIG. 10 is an illustration of a step in the application of a system according to an embodiment of the disclosure.
Figure 11:
FIG. 11 is an illustration of a step in the application of a system according to an embodiment of the disclosure.

FIGS. 10 and 11 illustrate the application of secondary strap 500 according to an embodiment of the disclosure. The figures show that toe strap 512 of secondary strap 500 extends from the distal end of the strap and is wrapped around the big toe.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A system for non-surgical treatment of plantar fasciitis, comprising:
    a primary support strap having a length and a width, the primary support strap being split lengthwise on a proximal end into two halves and split lengthwise on a distal end into two strips, the two strips having a narrower width than a width of the proximal end two halves and having a longer length than a length of the proximal end halves;
    a secondary support strap split at one end and adhesively attached to the primary support strap in a position wherein the lengths of the primary and secondary support straps are aligned, and the proximal end of the secondary support strap is oriented in a direction facing the proximal end of the primary support strap; and
    a cover support strap;
    wherein a combination of the primary, secondary, and cover support straps are configured to be applied to a foot such that the combination of straps provides dynamic windlass support to the foot.

2. The system of claim 1, wherein the support straps are comprised of elastic cotton tape having an initial elastic zone and a terminal stretch endpoint.

3. The system of claim 1, wherein the narrower width of the two strips of the primary support strap is formed by beveled edges extending from a start of the distal end split.

4. The system of claim 1, wherein the secondary support strap is split on the proximal end into two equal halves.

5. The system of claim 4, wherein the secondary support strap further comprises a toe strap extending from a distal end of the secondary support strap.

6. The system of claim 1, wherein the cover support strap is shorter in length than the primary or secondary support straps.

7. The system of claim 1, wherein the primary, secondary and cover support straps comprise an adhesive layer affixed to a backing paper removable prior to use.

8. The system of claim 1 wherein the secondary support strap has a length and a width, and the split is lengthwise on a proximal end thereof.

9. The system of claim 8 wherein:
    the cover support strap has a length that is longer than a width;
    the cover support strap is adhesively attached to the secondary support strap in a position wherein the length of the cover support strap is perpendicular to the length of the secondary support strap.

10. The system of claim 8, wherein the narrower width of the two strips of the primary support strap is formed by beveled edges extending from a start of the distal end split.

11. The system of claim 8, wherein the support straps are comprised of elastic cotton tape having an initial elastic zone and a terminal stretch endpoint.

12. A method of non-surgical treatment for of plantar fasciitis, comprising:
    applying a primary support strap to a foot, wherein the primary support strap has a length and a width, the primary support strap being split lengthwise on a proximal end into two halves and split lengthwise on a distal end into two strips, the two strips having a narrower width than a width of the proximal end two halves and having a longer length than a length of the proximal end halves;
    wherein the distal end of the primary support strap is placed at the metatarsal phalanges joint near the toes, the primary support strap is adhered along the length of the foot, and the proximal end of the primary support strap is placed near the heel;
    applying a secondary support strap to a foot, wherein the secondary support strap is split at one end and adhesively attached to the primary support strap along the length of the foot in a position wherein the lengths of the primary and secondary support straps are aligned, and the proximal end of the secondary support strap is oriented in a direction facing the proximal end of the primary support strap;
    wherein the distal end of the secondary support strap is applied across the metatarsal phalangeal joints at the ball of the foot, and a proximal end of the secondary support strap is placed at the heel; and
    applying a cover support strap to a foot, wherein the cover support strap is tensioned and adhered across the metatarsal phalanges joint in a direction perpendicular to the primary and secondary support straps.

13. The method of claim 12, wherein the primary, secondary, and cover support straps are first removed from backing paper to expose an adhesive layer prior to application.

14. The method of claim 12, wherein applying a primary support strap further comprises tensioning and wrapping the two strips on the distal end of the primary support strap around the foot and overlaying the two strips across the top of the foot and tensioning and wrapping proximal end halves the primary support strap loosely to the sides of the calcaneus.

15. The method of claim 12, wherein applying the secondary support strap further comprises tensioning and wrapping proximal end halves of the secondary support strap around the heel.

16. The method of claim 15, wherein applying the secondary support strap further comprises tensioning and wrapping a toe strap extending from the distal end of the secondary support strap around the toe.

17. The method of claim 12, wherein the secondary support strap is applied to the foot prior to application of the primary support strap.

18. The method of claim 12, wherein applying the primary and secondary support straps further comprises tensioning and adhering the primary and secondary support straps to the foot to achieve a desired level of flexibility and support of the straps.

19. A method of non-surgical treatment for of plantar fasciitis, comprising:
   applying a primary support strap to a foot, wherein the primary support strap has a length and a width, the primary support strap being split lengthwise on a proximal end into two halves and split lengthwise on a distal end into two strips, the two strips having a narrower width than a width of the proximal end two halves and having a longer length than a length of the proximal end halves
   wherein the distal end of the primary support strap is placed at the metatarsal phalanges joint near the toes, the primary support strap is adhered along the length of the foot, and the proximal end of the primary support strap is placed near the heel;
   applying a secondary support strap to a foot, wherein the secondary support strap is split at one end and adhesively attached to the primary support strap along the length of the foot in a position wherein the lengths of the primary and secondary support straps are aligned, and the proximal end of the secondary support strap is oriented in a direction facing the proximal end of the primary support strap;
   wherein the distal end of the secondary support strap is applied across the metatarsal phalangeal joints at the ball of the foot, a proximal end of the secondary support strap is placed at the heel;
   applying a cover support strap to a foot, wherein the cover support strap is tensioned and adhered across the metatarsal phalanges joint in a direction perpendicular to the primary and secondary support straps;
   wearing the primary, secondary, and cover support straps for at least one week; and
   replacing the primary, secondary, and cover supports straps every three to four days.

20. The method of claim 19, wherein the primary, secondary, and cover support straps are first removed from backing paper to expose an adhesive layer prior to application.

21. The method of claim 19, wherein applying a primary support strap further comprises tensioning and wrapping the two strips on the distal end of the primary support strap around the foot and overlaying the two strips across the top of the foot and tensioning and wrapping proximal end the primary support strap loosely to the sides of the calcaneus.

22. The method of claim 19, wherein applying the secondary support strap further comprises tensioning and wrapping proximal end halves of the secondary support strap around the heel.

23. The method of claim 22, wherein applying the secondary support strap further comprises tensioning and wrapping a toe strap extending from the distal end of the secondary support strap around the toe.

24. The method of claim 19, wherein applying the primary and secondary support straps further comprises tensioning and adhering the primary and secondary support straps to the foot to achieve a desired level of flexibility and support of the straps.

* * * * *